(12) United States Patent
Trokel

(10) Patent No.: US 10,058,270 B2
(45) Date of Patent: Aug. 28, 2018

(54) APPARATUS AND USE THEREOF FOR ANATOMICAL MAPPING OF A FACE

(71) Applicant: Yan Trokel, New York, NY (US)

(72) Inventor: Yan Trokel, New York, NY (US)

( * ) Notice: Subject to any disclaimer, the term of this patent is extended or adjusted under 35 U.S.C. 154(b) by 320 days.

(21) Appl. No.: 14/966,285

(22) Filed: Dec. 11, 2015

(65) Prior Publication Data
US 2016/0270695 A1 Sep. 22, 2016

Related U.S. Application Data

(60) Provisional application No. 62/136,009, filed on Mar. 20, 2015.

(51) Int. Cl.
*A61B 5/103* (2006.01)
*A61B 5/107* (2006.01)

(52) U.S. Cl.
CPC .......... *A61B 5/1077* (2013.01); *A61B 5/1072* (2013.01)

(58) Field of Classification Search
CPC .......................... A61B 5/1072; A61B 5/1077
USPC ............................................. 33/512; 600/587
See application file for complete search history.

(56) References Cited

U.S. PATENT DOCUMENTS

| | | | | |
|---|---|---|---|---|
| 6,327,787 B1* | 12/2001 | Bonzagni | ............ | A61B 5/1072 33/2 R |
| 8,276,288 B1* | 10/2012 | Yu | ........................ | A61B 5/1072 33/464 |
| 2005/0197598 A1* | 9/2005 | Von Rogov | .......... | A61B 5/1072 600/587 |
| 2006/0090360 A1* | 5/2006 | Shapiro | ..................... | B43L 7/10 33/473 |
| 2012/0302923 A1* | 11/2012 | Santiago | .............. | A61B 5/1072 600/587 |

* cited by examiner

*Primary Examiner* — Daniel Cerioni
(74) *Attorney, Agent, or Firm* — Norris McLaughlin & Marcus, P.A.

(57) ABSTRACT

A guide for anatomical mapping of a face includes two flexible strips arranged at right angles with one of the strips slidable in its lengthwise dimension relative to the other strip. The other strip is provided with an arcuate end edge and a window predetermined based on facial anatomical features. The width and intersection of the strips are predetermined based on facial anatomical features. The guide is arranged in various positions on the face of a subject and in each position markings are made on the face of the subject along edges and through the window of the guide. This facilitates, for example, locating safe and effective injection sites for filler and the like.

2 Claims, 8 Drawing Sheets

APPARATUS AND USE THEREOF FOR ANATOMICAL MAPPING OF A FACE

REFERENCE TO RELATED APPLICATION

Priority is claimed based on Provisional application Ser. No. 62/136,009, filed Mar. 20, 2015.

BACKGROUND OF THE INVENTION

The present invention relates to an apparatus in the form of a flexible guide which is particularly useful for anatomical mapping of a face. The invention also relates to use of the apparatus for the mapping. The mapping effected by the present invention is particularly useful for assistance with cosmetic non-surgical procedures, such as injection of facial fillers or injectable facial implants, and cosmetic surgical procedures, such as placement of solid facial implants and facial grafting of fat or synthetic materials.

SUMMARY OF THE INVENTION

A guide apparatus for anatomical mapping of a face according to the invention includes two rectangular strips which may be of substantially the same width, each sufficiently flexible to conform to facial contours.

One of the rectangular strips ("first rectangular strip") has one end edge ("first end edge") shaped as an arc approximating the shape of an infraorbital rim with each end of the arc together with a respective lengthwise edge of the first strip forming a point. The other end edge ("second end edge") of the first strip is rectilinear and forms right angled corners with the lengthwise edges of the first strip. The term "rectangular" as used herein with respect to the first strip refers to the overall shape of the strip without reference to the arcuate end edge as there is no more suitable term to characterize the shape of the strip.

The other rectangular strip ("second rectangular stip") is mounted to the first rectangular strip angularly fixedly at right angles to the first strip and slidably only in lengthwise directions of the second stip. The second strip has first and second end edges each of which is rectilinear and forms respective right angled corners with respective lengthwise edges of the second strip.

The first strip is of such width that, when the arcuate end edge is positioned on the infraorbital rim, one of the points at that edge abuts a tear trough and the other point abuts the lateral canthus of the same eye.

The second stip is, preferably, of substantially the same width as the first strip and may be of exactly the same width. It has been found that when the second strip is of exactly or substantially the same width as the first strip, both lengthwise edges of the second stip are also positioned appropriately for anatomical mapping of the face.

It will be apparent to one of ordinary skill in the art to which the present invention relates which anatomical terms refer to surface features of the face and which refer to features of the skull. To assure clarity, however, it is noted that "jawline", which may otherwise be ambiguous, in the present invention disclosure refers to the facial skeleton, and can be located by touch.

The first strip intersects the second strip at a position such that the guide is positionable against the face with, simultaneously, the corner of the second end edge of the first strip which is nearer than the other corner of the second end edge to the front of the face abutting the lateral canthus and an upper corner of one of the end edges of the second strip abutting the top of the crease at the lateral base of the nasal ala.

Preferably, the first strip also includes a rectangular window centered with respect to an imaginary lengthwise center line of the first strip. The rectangular window is preferably of greater dimension lengthwise than widthwise of the first strip. The distance between the window and the arcuate edge is such that the guide is positionable against the face with the imaginary center line of the first strip coincident with the center line of the face and the center of the arcuate edge abutting the philtrum and the points of the arcuate edge pointing upwardly, and, simultaneously, the window superposed on the mental protuberance. Preferably, the dimension of the window lengthwise of the first strip corresponds substantially to vertical dimension of the mental protuberance at the vertical center line of the mental protuberance.

A typical method, according to the invention, of using the apparatus is as follows.

Position the guide in a first position against the face with the arcuate end edge superposed on the infraorbital rim of an eye and one of the points of the arcuate end edge abutting a tear trough of the eye and the other of the points abutting a lateral canthus of the eye and lengthwise edges of the strip extending to the jawline. With the guide in the first position against the face, apply a marker to the face along the arcuate end edge, and along lengthwise edges of the first strip to respective end points at the jawline.

Position the guide in a second position against the face, with an upper corner, with respect to the face, of one of the rectilinear end edges of the second strip abutting a crease at a lateral base of a nasal ala and the first strip extending lengthwise downwardly to the jawline and the second strip extending lengthwise across a cheekbone and in alignment with an auricular helix. With the guide in the second position against the face, apply a marker to the face along lengthwise edges of the first and second strips.

If the aforementioned window has been provided in the guide, the guide is further capable of being used as follows in the anatomical mapping of the face.

Position the guide in a third position against the face with the arcuate edge centered with the philtrum of the upper lip and abutting a lower extremity of the philtrum and with the window superposed on the vertical dimension of the mental protuberance of the chin at the center line of the face. With the guide in the third position against the face, apply a marker to the face along the vertical extent of the window and along portions of the lengthwise edges of the first strip corresponding to locations or the chin laterally spaced from the mental protuberance.

The invention is described in further detail with reference to exemplary embodiments of the invention, with the aid of the following drawings.

DETAILED DESCRIPTION OF THE INVENTION

An exemplary embodiment of a flexible guide is made of two strips of flexible material, such as an elastomeric plastic or a natural or synthetic elastomer. Each of the strips has two parallel straight edges lengthwise of the strip. A first of the strips is made of two layers which are fastened or adhered to each other except for a length thereof slightly greater than the width of the second strip thereby forming a throughpassage which receives the second strip therethrough. The guide is assembled by inserting the second strip through the throughpassage of the first strip. Since the throughpassage is only slightly larger than the width of the second strip, the second strip can be slid relative to the first strip while being constrained to only right angles to the first strip. At times, when the guide is applied to a face, it may appear, due to facial contours, that the two strips are not perpendicular to each other though, in fact, they are. Friction between the second strip and the first strip assures that the second strip will remain fixed relative to the first strip unless an end portion of the second strip is gripped and pulled.

That the guide conforms to a non-planar surface in two directions at right angles to each other facilitates the mapping of zones or regions on the non-planar surface. The strips of the guide are preferably "flexible" in the sense of "pliable", i.e., foldable, so they will conform to contours.

Each of strips may be provided with markings and numbers (collectively, "indicia") indicating units and sub-units of measurement, such as centimeters and millimeters or inches and fractions of inches. For some applications, it is preferred that sets of indicia (i.e., "scales") be on both faces of the strips along both edges. If it is sufficient to map a surface, such as a face, without recording dimensions, scales may be dispensed with.

Specific embodiments of the guide may be configured for specialized use thereof. For example, the specific embodiment shown in the attached figures is for mapping a subject's face, especially for the purpose of aiding a practitioner of a cosmetic non-surgical procedure, for example, injections of filler into a subject's face. The invention will hereinbelow be described with reference to that embodiment.

Figure 1:
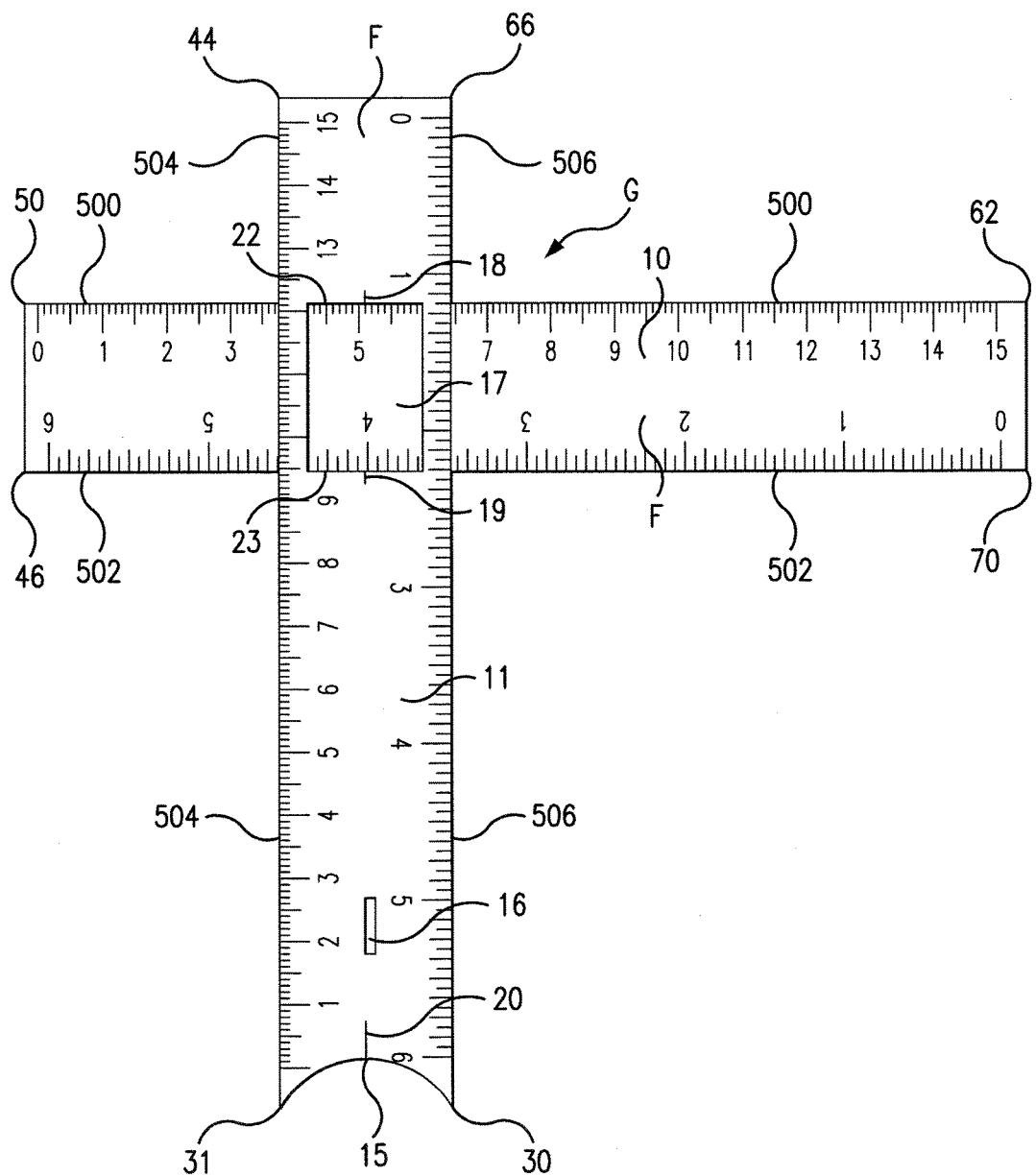
FIG. 1 is a plan view of the front face of a guide apparatus of the invention.
Figure 1A:
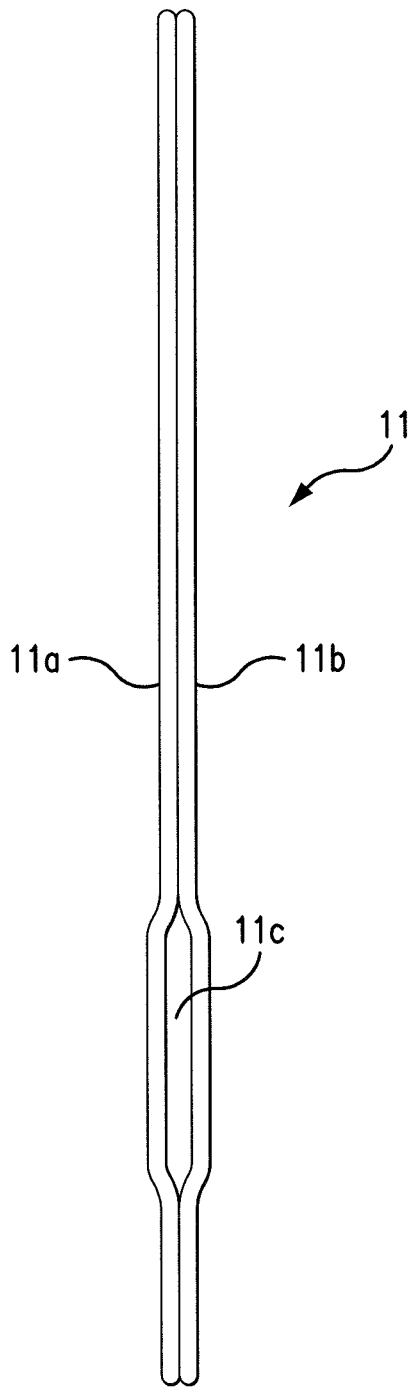
FIG. 1A is an edge view of one of the strips comprising the guide apparatus.
Figure 2:
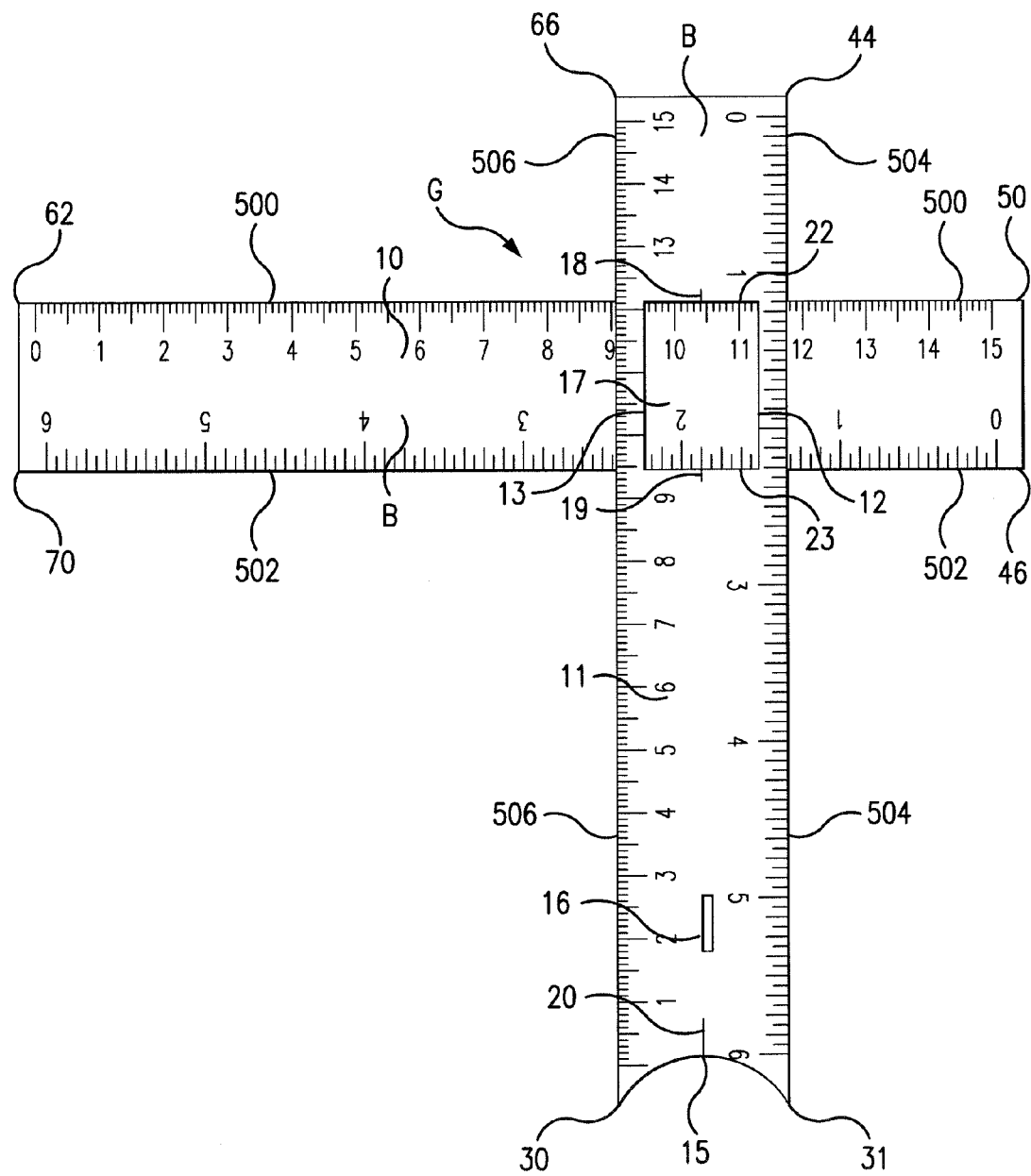
FIG. 2 is a plan view of the back face of a guide apparatus of the invention, it being understood that the terms "front" and "back" are arbitrary and interchangeable.
Figure 3:
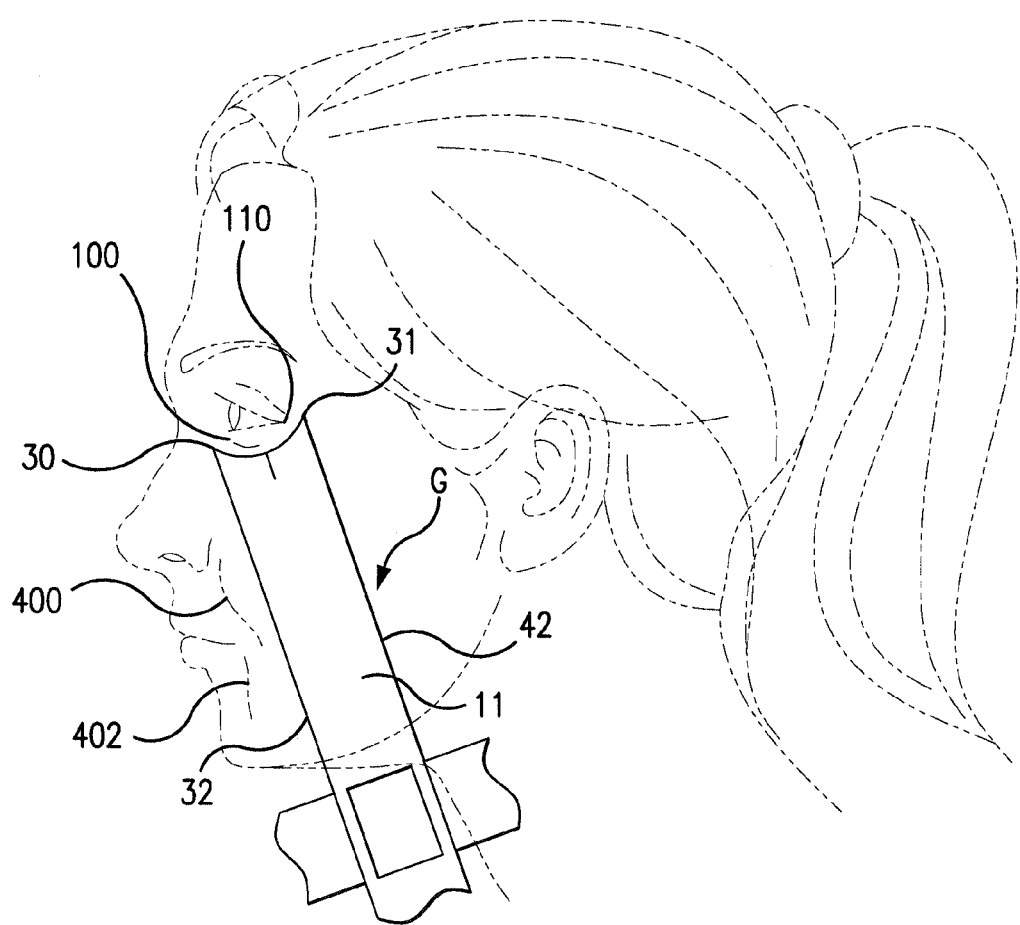
FIG. 3 is a profile view of a head showing a position of the guide apparatus in use for anatomical mapping of a face.

FIGS. 1 and 2 show front and back faces of an embodiment of a guide according to the invention for aiding a practitioner of cosmetic non-surgical procedures involving injections of fillers into a subject's face to locate appropriate injection sites (points, or zones or regions). The guide is constituted of a first flexible strip 11 and a second flexible strip 10 each preferably comprised of leather or natural or synthetic elastomer or of elastomeric or non-elastomeric plastic or of paper or cardboard, for example. The strips have parallel lengthwise edges 500, 502, 504 and 506. The strip 11 is comprised of two layers 11a and 11b (see FIG. 1A) which are fastened or adhered to each other (e.g., by stitching or by adhesive or by heat sealing), except for a length thereof slightly greater than the width of the stip 10 thereby forming a throughpassage 11c which receives the strip 10 therethrough. The strip 10 can be moved relative to the strip 11 by pulling on an end of the strip 10 to overcome friction between the strips 10 and 11 at their intersection, where they are in contact. Friction between the strips 10 and 11 prevents lengthwise displacement of the strip 10 relative to the strip 11 when neither end of the strip 10 is being pulled upon with sufficient force to overcome the aforementioned friction.

Numbers and markings are provided on both faces (front face F, back face B) of the strips 10 and 11 abutting each lengthwise edge of the strips 10 and 11. In the illustrated embodiment on each face of the strips 10 and 11 one edge is provided with a scale in centimeters and millimeters and the opposite edge is provided with a scale in inches and fractions thereof. Of course, these particular scales and that each edge has a scale different from the opposite edge are not requirements of the invention.

An end edge 15 of the strip 11 is provided with an arcuate configuration which is symmetrical relative to a lengthwise axis of symmetry of the strip 11. The arcuate edge 15 may be, for example, a circular arc of about 1.5-2 cm radius so as to approximate the shape of an edge portion of the orbital cavity formed by an upper edge of a lower portion of the zygomatic bone, i.e., the infraorbital rim. A window 16 generally of about 1 cm in length, to approximate the vertical dimension of the mental protuberance at the center line of a face, and about 1-2 mm in width, to accommodate the point of a marker, is formed through the strip 10 with the midpoint of the window 16 a distance generally of about 2 cm from the midpoint of the arcuate edge 16 to approximate the distance between the lower extremity of the philtrum and the vertical center of the mental protrusion at the facial center line, i.e., the center of the mental protuberance. The other end edges of the strips 10, 11 are rectilinear and form right angled corners with the lengthwise edges of the strip. Each meeting of a lengthwise edge with a rectilinear end, i.e., widthwise, edge forms a respective point 44, 66, 50, 40, 62, 70. A rectangular window 17 is formed through the strip 11, where the throughpassage 11c is located. The window is essentially of the same dimension lengthwise of the strip 11 as the width of the strip 10 so that the scales at the edges 500, 502 of the strip 10, are visible on both faces F and B of the guide G. On an imaginary lengthwise center line on both faces F and B of the strip 11 are inscribed lengthwise markings 18, 19, adjacent the scales visible at the window 17 of the strip 10, and lengthwise marking 20, at the midpoint of the arcuate edge 15.

The window 17 is symmetrical with respect to an imaginary lengthwise center line on the strip 11. Top 22 and bottom 23 edges of the window 17 are immediately adjacent top and bottom edges of the strip 10 so that the scales adjacent both lengthwise edges of the strip 10 are visible through the window 17. The window is of sufficient width so that a number and the markings of the scales can be seen through the window. At the top and bottom edges 22, 23 of the window 17 on the imaginary lengthwise center line are inscribed lengthwise markings 18 and 19, respectively, on both faces.

The markings 18, 19 are for the purpose of facilitating measurement of distances. The second strip 10 intersects the first strip 11 at a location such that the guide is positionable against the face with, simultaneously, the corner 44 of the first strip 11 abutting a lateral canthus 210 and a corner 50 of the second strip abutting the crease 108 at the lateral base of the ala. It is convenient that each of the strips 10 and 11 be about 15 cm long in order that the practitioner need not manipulate excess lengths of strips 10 and 11. The strips 10 and 11 are about 3-4 cm wide.

The embodiment of the guide G shown in FIGS. 1A and 2 is especially adapted for assisting a practitioner in locating injection sites for injection of filler. With the aid of the guide, lines and other markings are applied to the face of the patient with a washable marker to locate filler injection sites (points, or areas or zones) suitable for aesthetically optimum enhancement of the appearance of the patient's face while avoiding nerves and blood vessels. Both lengthwise edges of the strips 10, 11 are used to draw lines on the patient's face. Apart from being used to map portions of the face including a portion of the orbit of each eye, the arcuate edge 15 of the guide is placed against the patient's face with the arcuate edge 15 abutting, and the mark 20 centered at, the base of the notch (philtrum or "cupid's bow") at the center of the upper lip, and the patient's chin area is mapped for determining filler injection sites by making markings on the chin through the window 16 as well as with the lengthwise edges of the strip 11.

The numerical dimensions mentioned hereinabove for the guide G are based upon use of the guide G on a typical adult face. Because a guide of the invention may also be dimensioned for an atypical face or for a child's face, the dimensions are most meaningfully defined in terms of the ability to position the guide with points thereof simultaneously at facial features as specified herein.

In the following written description and FIGS. 3-7 are described typical use of the flexible guide of the invention for mapping facial zones. Use of the guide is illustrated for one side of the face. It is understood that the device is likewise used for the other side of the face. The guide is manipulated and held on the face by the practitioner. It is apparent that the practitioner will generally hold the guide in place with his/her fingertips. In order to provide unobstructed views, the practitioner's hands are not shown in the drawings. Also, in FIGS. 3, 5 and 6 the guide is shown somewhat schematically for the sake of clarity of illustration.

Figure 4:
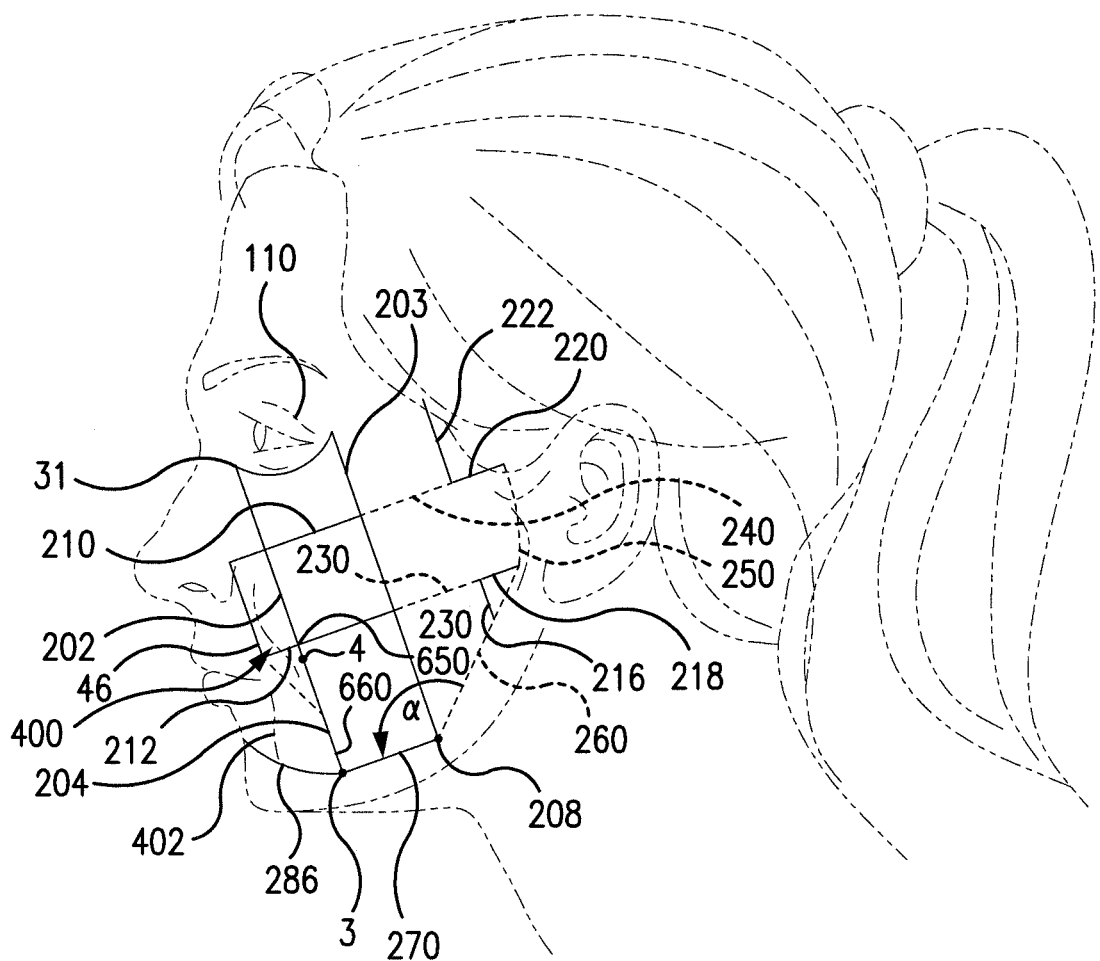
FIG. 4 is a profile view of the head showing an example of anatomical mapping of the face effected by use of the guide apparatus.
Figure 5:
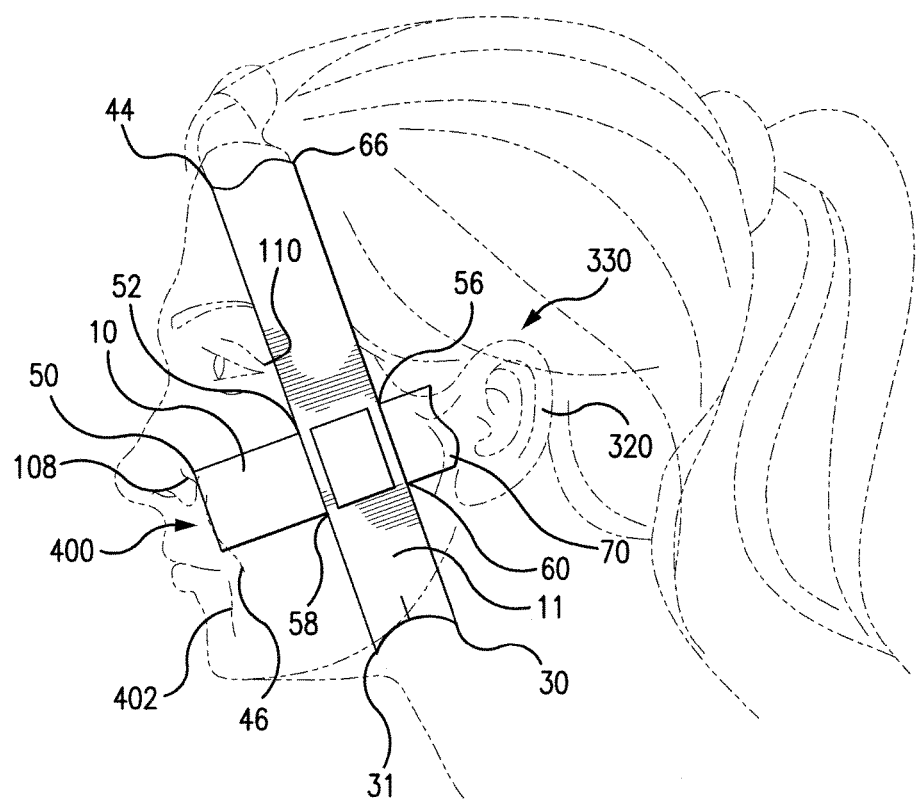
FIG. 5 is a profile view of the head showing another position of the guide apparatus in use for anatomical mapping of a face.

In a step 1 (FIG. 3), the practitioner locates the subject's infraorbital rim by means of his/her fingertips and places the center of the guide G arcuate edge 15, which is indicated by the marking 20, on the infraorbital rim with point 30 at one end of the arcuate edge 15 abutting the tear trough 100 and point 31 at the other end of the arcuate edge 15 abutting the lateral canthus 110 with the lengthwise edges 32, 42 of the guide G substantially parallel to the subject's nasolabial fold 400. Using the arcuate edge 15 as a guide, the practitioner draws with a marker an arcuate line 200 at the infraorbital rim (FIG. 4). Using the lengthwise edge 32 of the guide, the practitioner draws a line 202 ("medial line") from the point 30 of the guide G, abutting the subject's tear trough 100 to a point 3 at the jawline (FIG. 4). Using the lengthwise edge 42 of the guide G, the practitioner draws a line 203 from the point 31 to a point 208 at the jawline.

In a step 2 (FIG. 5), the practitioner repositions the guide G with the strips 10, 11 arranged so that corner point 44 of the strip 11 abuts the lateral canthus 110 and corner point 50 of the strip 10 abuts the crease 108 at the lateral base of the ala of the nose. The strip 10 is aligned with the helix 320 of the auricle 330. The practitioner draws line 210 using the edge extending between points 50 and 52, line 212 using the edge extending between points 46 and 58, line 204 using the edge between points 58 and 31, line 216 using the edges between points 60 and 30, line 218 using the edge between points 60 and 70, line 220 using the edge between points 56 and 62 (point 62 abutting the end of the zygomatic arch), and line 222 using the edge between points 56 and 66. Points on edges are used to identify edges, and if the point on an edge is beyond the subject's face, the line drawn using the edge does not extend to that point. Line 240 connecting lines 210 and 320 and line 230 connecting lines 212 and 218 would generally be drawn as solid lines but are shown as broken lines merely to indicate that they are drawn with a straight edge such as a straight edge of the guide G to complete step 3 after the guide G has been moved away from its position on the subject's face shown in FIG. 5. The same applies to other broken lines in the drawings.

The mapping thus far provides valuable information for cosmetic non-surgical and surgical procedure planning. For example, the line between point 46 and intersection 550 approximates an upper extremity of the buccal area, the lines 210, 240, 220 approximate the upper extremity of the cheekbone and the lines 212, 230, 218 approximate the lower extremity. The intersection of lines 203 and 240 approximates the highest point of the cheek. The line from point 30 to point 3 at the jawline is the medial line. A line drawn from point 46 to point 660 on the medial line at a level substantially corresponding to the level of the top of the mental protuberance completes a triangle defining the buccal area. Point 3 is an insertion point of the jawline for injection of filler, for filling "marionette lines" 402 for example. Point 4 on the medial line and proximate the nasolabial fold is another insertion point for injection of filler, for filling in nasolabial fold in 400. The angle α between a line 260 drawn with a straight edge from the end of a line 218 adjacent the subject's auricle to point 208 and a line 270 drawn between points 208 and 204 approximates the mandibular angle. The ramus is approximately bounded in part by lines, 203, 230, 218, 260. The length of line 250, extending between the lines 218 and 220 adjacent the auricle 320 is the height of the ramnus.

It is to be understood that the drawings herein are two-dimensional whereas the face is three-dimensional. The guide, in practice, conforms to the curvatures of the face. Therefore, the drawings show an approximation of how the guide lies on the face and the resulting lines. In any event, following the procedures as described herein will result in a mapping of a subject's face of practical use to a practitioner of cosmetic procedures involving alteration of facial contours.

Steps 1 and 2 have been illustrated and described for only one side of the face. These steps will generally be carried out on both sides of the face. It is particularly convenient to flip the guide over after doing each of steps 1 and 2 on one side of the face to do the same step on the other side of the face since the opposite sides of the subject's face and the opposite faces ("front" and "back") of the guide are mirror images of each other in shape (apart from any, generally minor, facial asymmetries). However, the steps of the method of the invention, including hereinafter described step 3, may be carried out in any order and without alternating from one side of the face to the other.

Anatomical mapping of a face according to the invention is a very efficient way to identify appropriate sites for non-surgical and surgical facial recontourings. Moreover, once steps 1 and 2 have been carried out on both sides of a face, visually comparing the markings on each side of the face with those on the other side, such as by looking at the face head-on, reveals any asymmetries.

Figure 6:
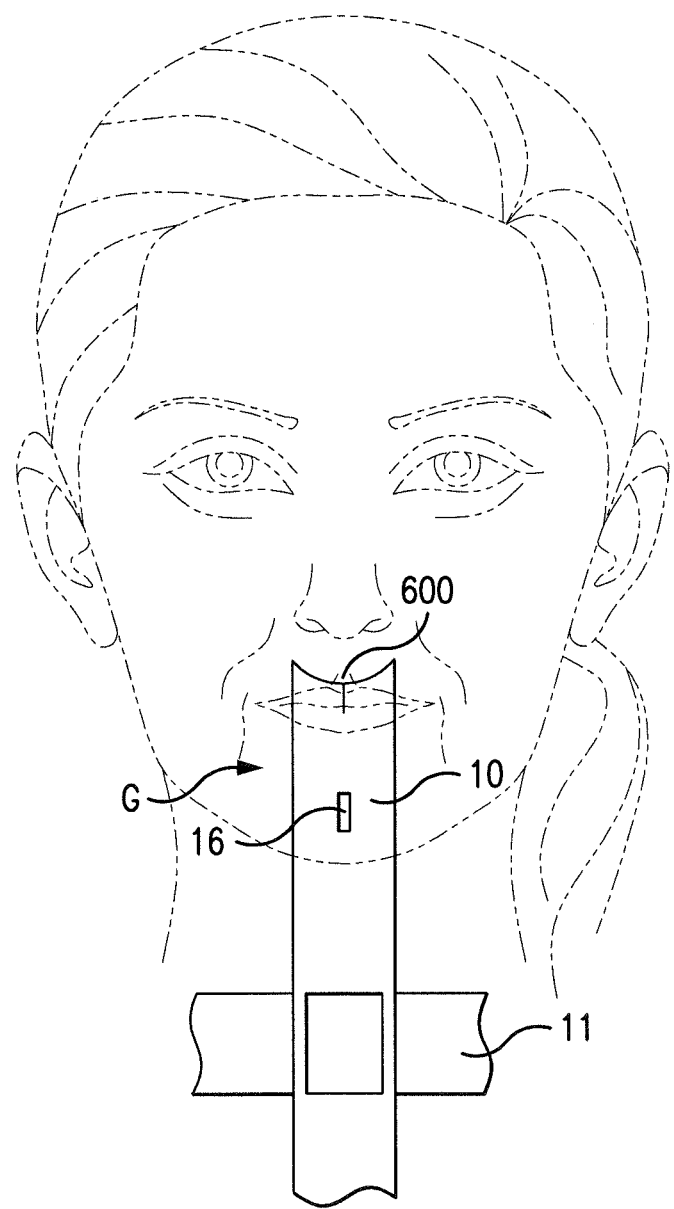
FIG. 6 is a front view of the head showing yet another position of the guide apparatus in use for anatomical mapping of a face.
Figure 7:
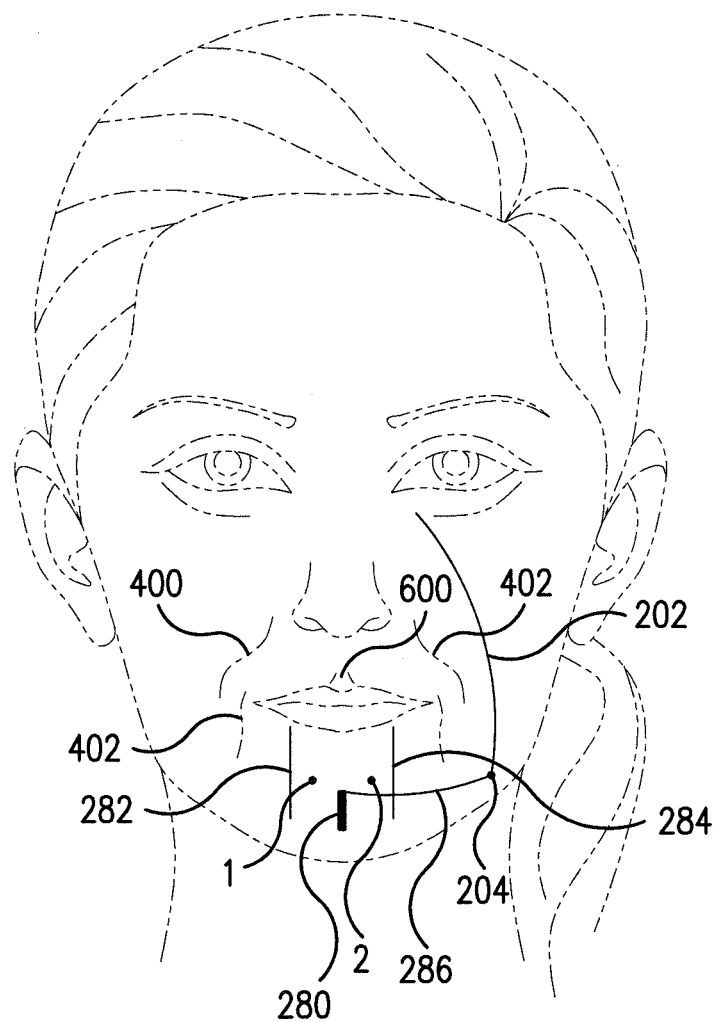
FIG. 7 is a front view of the head showing additional anatomical mapping of the face effected by use of the guide apparatus.

Step 3 is illustrated by means of front views (FIGS. 6 and 7) of the face together with FIG. 4. Application of the guide G is illustrated in FIG. 6 and the markings made are illustrated in FIG. 7. For convenience and clarity, markings made in steps 1 and 2 are not shown in FIGS. 6 and 7 with the following exception. One of the lines made in step 1, including a lower endpoint 3 thereof at the jawline, is shown in FIG. 7 in order to show its being connected at the lower endpoint 3 thereof to a line drawn in step 3.

In step 3, the guide G is positioned with the strip 10 vertically centered with respect to the subject's face and the center mark 20 of the arcuate edge abutting the lower extremity (base) of the notch 600 of the subject's upper lip (the notch being known as the philtrum or "cupid's bow"). The practitioner makes a vertical marking 280 (FIG. 7) through the window 16 corresponding to the location and vertical dimension of the window 16, i.e., substantially corresponding to the vertical dimension of the mental protuberance at the center line of the face, and also makes vertical lines 282, 284 using lengthwise edges of an end portion the strip 11 below the subject's lower lip. Repositioning the guide G and using an edge of the guide G, the practitioner then draws a line 286 between the upper end of the mark 280 and the lower end point 3 of the line 202 (FIGS. 4, 7). This is repeated (not shown) with respect to the other side of the face.

Just by way of example, points 1 and 2 are safe and appropriate for injection of filler in the subject's chin, and point 3 is safe and appropriate for injection of filler at the jawline, for example to cosmetically treat (fill in) the "marionette lines" 402, and point 4 is safe and appropriate for injection of filler to cosmetically treat (fill in) nasolabial folds 400.

The guide G can be manipulated in other ways, for example, in connection with locating sites suitable for, for example, injection of filler around the eyes, particularly considering that the arcuate edge, which approximately conforms to the infraorbital rim, facilitates mapping a face in areas abutting the eyes in order to locate sites suitable for injection of fillers in those areas.

The invention claimed is:

1. A method for anatomical mapping of a face with an apparatus comprising
    first and second rectangular strips of substantially a same width and each sufficiently flexible to conform to facial contours and having rectilinear lengthwise edges, wherein
    the first rectangular strip has a first end edge shaped as an arc approximating a shape of an infraorbital rim, each end of the arc together with a respective one of the lengthwise edges of the first strip forming a respective point, and a second end edge which is rectilinear and forms right angled corners with the lengthwise edges of the first strip;
    the second rectangular strip is mounted to the first strip angularly fixedly at right angles to the first strip and slidably only in lengthwise directions of the second strip and has first and second end edges each of which is rectilinear and forms a respective right angled corner with a respective one of the lengthwise edges of the second strip,
    the first strip is of such width that, when the arcuate end edge is positioned on an infraorbital rim of an eye, one of the points of the arcuate end edge abuts a tear trough of the eye and the other point abuts a lateral canthus of the eye, and
    the second strip intersects the first strip at a location such that the guide is positionable against the face with, simultaneously, the corner of the second end edge of the first strip which is nearer than the other corner of the second end edge of the first strip to a front of the face abutting the lateral canthus, and an upper corner of one of the end edges of the second strip abutting a lateral crease of an ala,
the method comprising
positioning the apparatus in a first position against the face with the arcuate end edge superposed on an infraorbital rim of an eye and one of the points of the arcuate end edge abutting a tear trough of the eye and the other of the points abutting a lateral canthus of the eye and lengthwise edges of the first strip extending to a jawline,
with the apparatus held in the first position against the face, applying a marker to the face along the arcuate end edge and along lengthwise edges of the first strip to respective end points abutting the jawline,
positioning the apparatus in a second position against the face, with an upper corner, with respect to the face, of one of the rectilinear end edges of the second strip abutting a crease at a lateral base of a nasal ala and a forward corner, with respect to the face, of the first strip abutting a lateral canthus of the eye, and the first strip extending lengthwise downwardly to a jawline and the second strip extending lengthwise across a cheekbone and in alignment with an auricular helix, and
with the apparatus held in the second position against the face, applying a marker to the face along lengthwise edges of the first and second strips.

2. A method for anatomical mapping of a face with an apparatus comprising
    first and second rectangular strips of substantially a same width and each sufficiently flexible to conform to facial contours and having rectilinear lengthwise edges, wherein
    the first rectangular strip has a first end edge shaped as an arc approximating a shape of an infraorbital rim, each end of the arc together with a respective one of the lengthwise edges of the first strip forming a respective point, and a second end edge which is rectilinear and forms right angled corners with the lengthwise edges of the first strip;
    the second rectangular strip is mounted to the first strip angularly fixedly at right angles to the first strip and slidably only in lengthwise directions of the second strip and has first and second end edges each of which is rectilinear and forms a respective right angled corner with a respective one of the lengthwise edges of the second strip,
    the first strip is of such width that, when the arcuate end edge is positioned on an infraorbital rim of an eye, one of the points of the arcuate end edge abuts a tear trough of the eye and the other point abuts a lateral canthus of the eye,
    the first strip further comprises a rectangular window centered with respect to an imaginary lengthwise center line of the first strip, and
    the window is located at such position along the length of the first strip that when the arcuate end edge is centered at a base of an upper lip philtrum with the points of the edge pointing upwards, the window is superposed on a mental protuberance, and
    the second strip intersects the first strip at a location such that the guide is positionable against the face with, simultaneously, the corner of the second end edge of the first strip which is nearer than the other corner of the second end edge of the first strip to a front of the face abutting the lateral canthus, and an upper corner of one of the end edges of the second strip abutting a lateral crease of an ala, the method comprising positioning the apparatus in a first position against the face with the arcuate end edge superposed on an infraorbital rim of an eye and one of the points of the arcuate end edge abutting a tear trough of the eye and the other of the points abutting a lateral canthus of the eye and lengthwise edges of the first stip extending to a jawline, with the apparatus held in the first position against the face, applying a marker to the face along the arcuate end edge and along lengthwise edges of the first strip to respective end points abutting the jawline, positioning the apparatus in a second position against the face, with an upper corner, with respect to the face, of one of the rectilinear end edges of the second strip abutting a crease at a lateral base of a nasal ala and a forward corner, with respect to the face, of the first strip abutting the lateral canthus of the eye, and the first strip extending lengthwise downwardly to the jawline and the second strip extending lengthwise across a cheekbone and in alignment with an auricular helix, with the apparatus held in the second position against the face, applying a marker to the face along lengthwise edges of the first and second strips, positioning the apparatus in a third position against the face with the arcuate edge centered with a philtrum of an upper lip and abutting a lower extremity of the philtrum and with the window superposed on a vertical dimension of a mental protuberance of a chin at a center line of the face, and with the apparatus held in the third position against the face, applying a marker to the mental protuberance along a vertical extent of the window and along portions of the lengthwise edges of the first strip corresponding to locations on the chin laterally spaced from the mental protuberance.

\* \* \* \* \*